United States Patent
Higuchi

(10) Patent No.: US 11,478,147 B2
(45) Date of Patent: Oct. 25, 2022

(54) OPTOMETRY SYSTEM AND STORAGE MEDIUM

(71) Applicant: NIDEK CO., LTD., Aichi (JP)

(72) Inventor: Yukihiro Higuchi, Aichi (JP)

(73) Assignee: NIDEK CO., LTD., Aichi (JP)

( * ) Notice: Subject to any disclaimer, the term of this patent is extended or adjusted under 35 U.S.C. 154(b) by 404 days.

(21) Appl. No.: 16/698,208

(22) Filed: Nov. 27, 2019

(65) Prior Publication Data

US 2020/0170506 A1 Jun. 4, 2020

(30) Foreign Application Priority Data

Dec. 3, 2018 (JP) .............................. JP2018-226277
Dec. 3, 2018 (JP) .............................. JP2018-226278

(51) Int. Cl.
*A61B 3/14* (2006.01)
*A61B 3/00* (2006.01)
*A61B 3/10* (2006.01)
*A61B 3/12* (2006.01)

(52) U.S. Cl.
CPC ............ *A61B 3/145* (2013.01); *A61B 3/0041* (2013.01); *A61B 3/0083* (2013.01); *A61B 3/102* (2013.01); *A61B 3/12* (2013.01)

(58) Field of Classification Search
CPC ..... A61B 3/145; A61B 3/0041; A61B 3/0083; A61B 3/102; A61B 3/12; A61B 3/0016
USPC ......................................................... 351/208
See application file for complete search history.

(56) References Cited

U.S. PATENT DOCUMENTS

| | | |
|---|---|---|
| 5,767,940 A | 6/1998 | Hayashi et al. |
| 2007/0222945 A1* | 9/2007 | Tsukada .................. A61B 3/102 351/205 |
| 2010/0110171 A1 | 5/2010 | Satake |
| 2013/0258283 A1* | 10/2013 | Goto ......................... A61B 3/14 351/206 |
| 2015/0168127 A1* | 6/2015 | Takeno ................ A61B 5/0066 356/479 |
| 2015/0190047 A1* | 7/2015 | Sugiura .................. G16H 40/63 351/233 |
| 2019/0275833 A1* | 9/2019 | Stuck ......................... B60B 3/00 |

FOREIGN PATENT DOCUMENTS

| | | |
|---|---|---|
| JP | 5-176893 A | 7/1993 |
| JP | 10-33479 A | 2/1998 |
| JP | 2010-110392 A | 5/2010 |

* cited by examiner

*Primary Examiner* — Mohammed A Hasan
(74) *Attorney, Agent, or Firm* — Sughrue Mion, PLLC

(57) ABSTRACT

An optometry system for examining a subject eye of an examinee includes an optometry device for examining the subject eye, an imaging unit that captures an image of an examination room including the examinee and the optometry device, and a remote operation unit that includes a display unit which displays an operation screen for operating the optometry device and an captured image captured by the imaging unit, and a display control unit which controls display of the display unit to display the operation screen and the captured image on the display unit. The remote operation unit enables an examiner to observe the captured image displayed on the display unit to guide the examinee to an examination position.

14 Claims, 7 Drawing Sheets

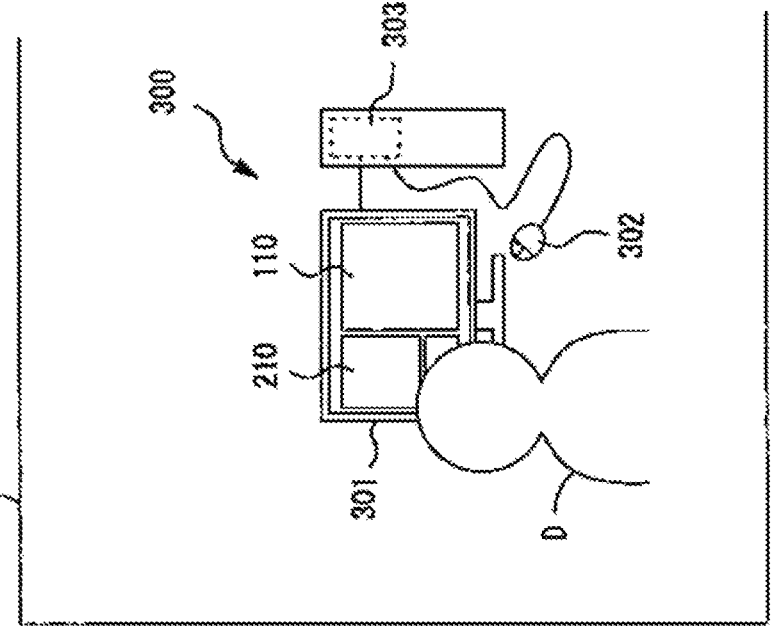
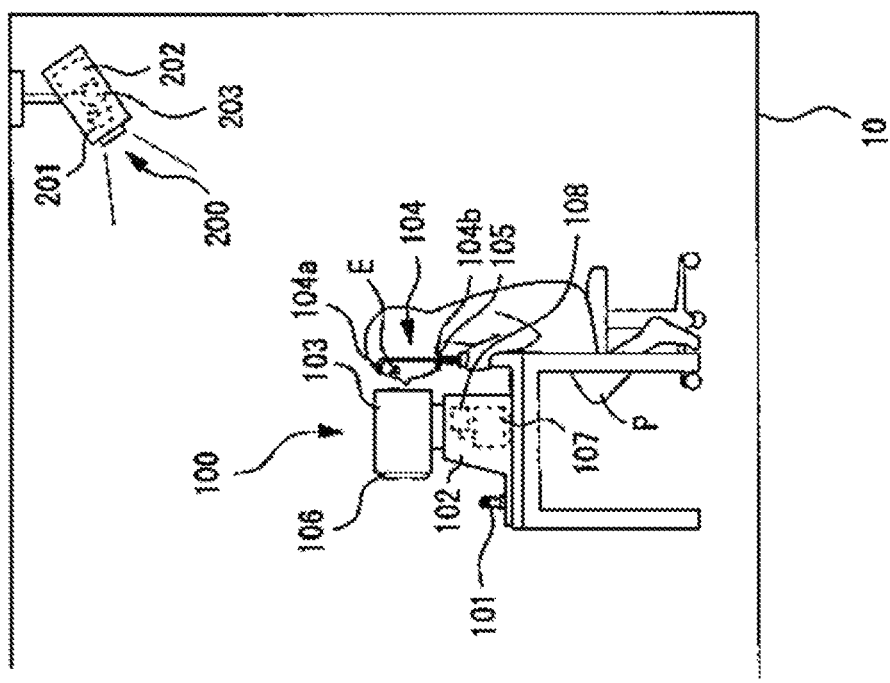
FIG. 2

OPTOMETRY SYSTEM AND STORAGE MEDIUM

CROSS-REFERENCE TO RELATED APPLICATION

This application claims priority from Japanese Patent Applications No, 2018-226277 filed on Dec. 3, 2018 and No. 2018-226278 filed on Dec. 3, 2018, the entire subject-matter of which is incorporated herein by reference.

TECHNICAL FIELD

The present disclosure relates to an optometry system and a storage medium storing an optometry program for examining a subject eye of an examinee.

BACKGROUND

As an optometry device that examines a subject eye, a subjective optometry device (JP-A-H05-176893) that subjectively measures optical characteristics of the subject eye, an objective optometry device that objectively measures the optical characteristics of the subject eye (JP-A-H10-33479), and an ophthalmologic imaging device that images a fundus tomographic image of the subject eye (JP-A-2010-110392) are used.

An examiner guides the examinee to the optometry device such that the examinee is placed at an examination position for optometry of the subject eye and starts the optometry. Further, the examiner examines the subject eye by directly operating the optometry device.

However, there is a case where it is difficult for an examinee to go to a distant facility for optometry. Therefore, a mechanism that can easily perform the optometry is desired. Further, there is a case where an examiner performs the optometry by using a plurality of devices in various places such as a bright room and a dark room. Therefore, a mechanism capable of efficiently examining many examinees is desired. Accordingly, the inventor reviewed a mechanism by which the examiner performs the optometry through a remote operation.

As a first problem, since the examiner and the examinee are separated from each other in a case where a remote operation is performed, it is considered that it is difficult for the examiner to guide the examinee to a state where examination can be started. Further, it is considered that it takes time to start the examination because it is difficult to guide the examinee.

As a second problem, for example, since an operation procedure is changed depending on presence or absence of an assistant who assists the examinee in a case where a remote operation is performed, an appropriate setting according to various operation procedures is required.

SUMMARY

An object of the present disclosure is to provide an optometry system and a storage medium storing an optometry program that can easily perform optometry even if an examiner and an examinee are separated from each other.

In order to achieve the above object, the present disclosure includes the following configurations.

(1) An optometry system for examining a subject eye of an examinee, including:
 an optometry device configured to examine the subject eye;
 an imaging unit configured to capture an image of an examination room including the examinee and the optometry device; and
 a remote operation unit including:
 a display unit configured to display an operation screen for operating the optometry device and an captured image captured by the imaging unit; and
 a display control unit configured to control display of the display unit to display the operation screen and the captured image on the display unit,
 in which the remote operation unit enables an examiner to observe the captured image displayed on the display unit to guide the examinee to an examination position.

(2) The optometry system according to the above-described (1),
 in which the display control unit displays the operation screen and the captured image on the same screen of the display unit.

(3) The optometry system according to the above-described (1), further including:
 a signal acquisition unit configured to acquires a switching signal for switching between the operation screen and the captured image,
 in which the display control unit switches a screen to be displayed on the display unit between the operation screen and the captured image based on the switching signal.

(4) The optometry system according to the above-described (1),
 in which the imaging unit includes a night vision camera that images the examination room under night vision and enables the examination room to be imaged under the night vision.

(5) The optometry system according to the above-described (1),
 in which the optometry device includes:
 a determination unit configured to determine whether or not the subject eye is in an examinable state; and
 a first output unit configured to output determination information based on a determination result of the determination unit.

(6) The optometry system according to the above-described (1),
 in which the optometry device includes:
 a determination unit configured to determine whether or not the subject eye is in an examinable state; and
 a second output unit configured to output an instruction signal for instructing a next operation to at least one of the optometry device and the remote operation unit based on a determination result of the determination unit.

(7) The optometry system according to the above-described (5),
 in which the optometry device includes:
 a jaw rest for placing a jaw of the examinee; and
 a detection unit configured to detect whether or not the jaw of the examinee is placed on the jaw rest.
 in which the determination unit determines whether or not the subject eye is in an examinable state based on a detection result of the detection unit.

(8) A non-transitory computer readable recording medium storing an optometry program executed in an optometry system for examining a subject eye of an examinee,
 the optometry program is executed by a processor in the optometry system to cause the optometry system to perform:
 an imaging step of capturing an image of an examination room including the examinee and the optometry device;

a display control step of controlling display of a display unit included in a remote operation unit to display an operation screen for operating the optometry device and a captured image captured by an imaging unit on the display unit; and a remote operation step of enabling an examiner to observe the captured image displayed on the display unit to guide the examinee to an examination position.

(9) An optometry system for examining a subject eye of an examinee, including:

an optometry device configured to examine the subject eye;

a first operation unit provided in a housing of the optometry device or near the optometry device and configured to operate the optometry device;

a second operation unit provided apart from the optometry device and configured to operate the optometry device;

a first setting unit configured to assign a first operation of the optometry device to a first operation signal input from the first operation unit; and a second setting unit configured to assign a second operation of the optometry device to a second operation signal input from the second operation unit

(10) The optometry system according to the above-described (9), further including:

an operation control unit configured to prohibit, when an operation of the optometry device according to one of the first operation signal and the second operation signal is performed; an operation of the optometry device according to the other of the first operation signal and the second operation signal from being performed.

(11) The optometry system according to the above-described (9), in which the optometry device includes a fundus imaging unit configured to image a fundus of the subject eye, and at least one of the first setting unit and the second setting unit assigns an operation for starting imaging by the fundus imaging unit to the operation signal.

(12) The optometry system according to the above-described (9), in which the optometry device includes an alignment unit configured to align the subject eye and the optometry device, and at least one of the first setting unit and the second setting unit assigns an operation for performing alignment by the alignment unit to the operation signal.

(13) The optometry system according to the above-described (9), further including:

an information acquisition unit configured to acquire operator information indicating an operator who operates the optometry device;

a display unit configured to display the operator information; and a display control unit configured to cause the display unit to display the operator information.

BRIEF DESCRIPTION OF DRAWINGS

FIG. 2 is a use example of the optometry system.

DETAILED DESCRIPTION

<Overview>

Figure 1:
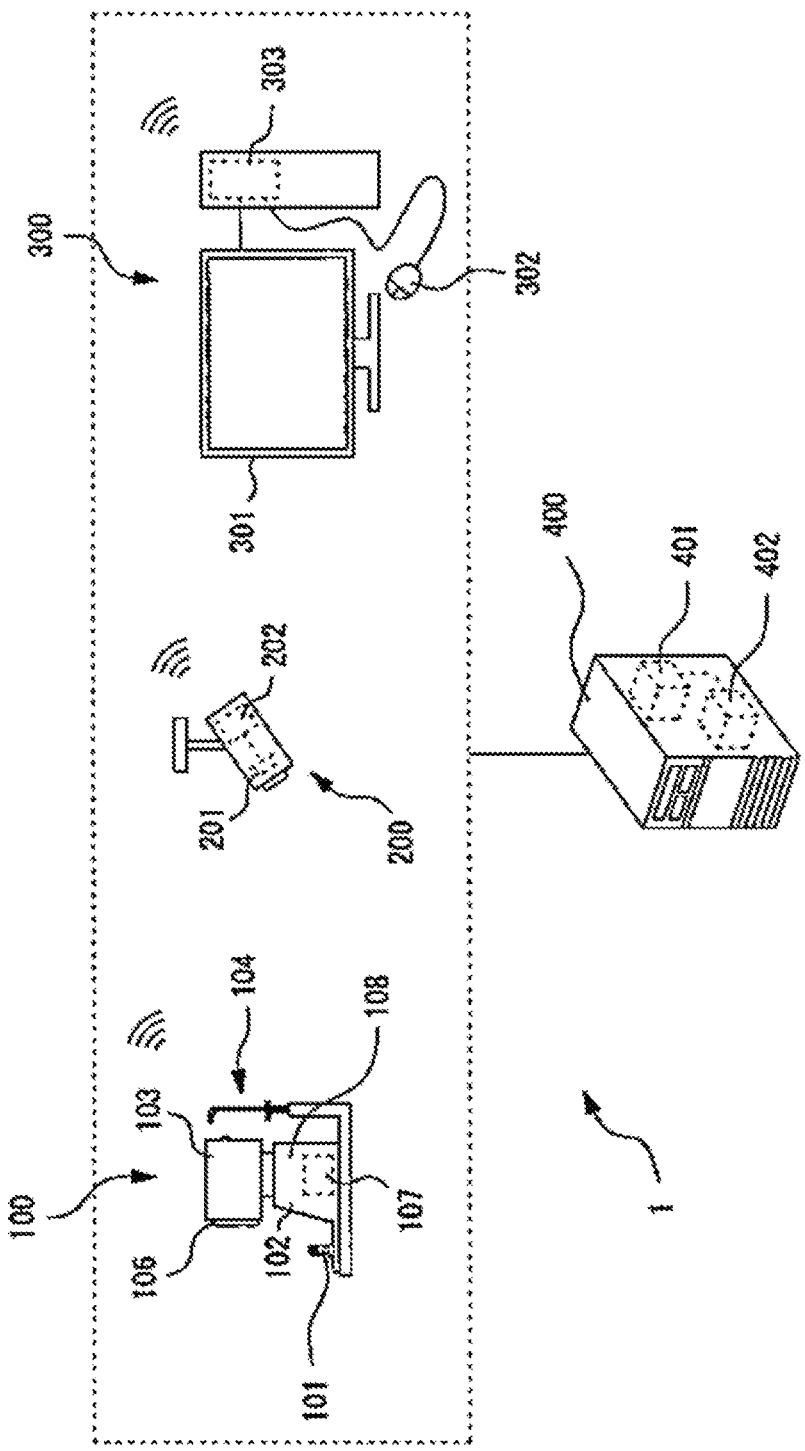
FIG. 1 is a schematic diagram of an optometry system.

An outline of the embodiment according to the present disclosure will be described. Items classified as < > below can be used independently or in association with each other.

An optometry system (for example, an optometry system 1) according to the present embodiment is an optometry system for examining a subject eye of an examinee. As an example, the subject eye may be measured by using an optometry system. Further, as an example, the subject eye may be imaged by using the optometry system.

Such an optometry system may be an optometry system for measuring optical characteristics of the subject eye. For example, as the optical characteristics of the subject eye, eye refractive power (for example, spherical power, cylindrical power, astigmatic axis angle, or the like), an eye axial length, a corneal shape, and the like of the subject eye may be measured subjectively. Further, for example, as the optical characteristics of the subject eye, the eye refractive power, contrast sensitivity, a binocular vision function (for example, an oblique amount, a stereoscopic vision function, or the like), and the like of the subject eye may be measured subjectively. Further, such an optometry system may be an optometry system for measuring a visual field of the subject eye by obtaining a response by visual recognition of the examinee.

Further, such an optometry system may be an optometry system for imaging an anterior eye portion and a fundus of the subject eye. For example, anterior eye portion image data, a cornea shape, and the like of the subject eye may be acquired by imaging the anterior eye portion of the subject eye. Further, fundus front image data, tomographic image data, and the like of the subject eye may be acquired by imaging the fundus of the subject eye.

<Imaging of Examination Room and Examination Using Optometry Device>

In the present embodiment, the optometry system includes an optometry device (for example, an OCT device 100). The optometry device examines the subject eye. Examples of the optometry device include a subjective optometry device that subjectively measures optical characteristics of the subject eye, an objective optometry device that objectively measures the optical characteristics of the subject eye, and a visual field meter that measures a visual field of the subject eye, an ophthalmologic imaging device that images a fundus tomographic image of the subject eye, and the like.

In the present embodiment, the optometry device may include a communication unit. The optometry device communicates with other configuration elements (for example, an imaging unit, a remote operation unit, and the like) of the optometry system by using the communication unit. The communication unit may communicate with other configuration elements by using a configuration of at least one of a wired communication and a wireless communication. For example, in a case of the wired communication, an optical fiber, a wired LAN, or the like may be used. For example, in a case of the wireless communication, the Wi-Fi (registered trademark), the Bluetooth (registered trademark), or the like may be used. The communication unit may include a reception unit and a transmission unit. The reception unit and the transmission unit may be shared or may be provided separately.

The optometry system according to the present embodiment may be configured such that the optometry device directly communicates with other configuration elements via the communication unit. Further, the optometry system according to the present embodiment may include a shared server (for example, the shared server 400), and the optometry device may indirectly communicate with other configuration elements from the communication unit via the shared server. That is, the optometry device and other configuration elements may be connected via a shared server.

<Detection Unit>

In the present embodiment, the optometry device includes a detection unit (for example, a detector 105). The detection unit may detect a contact between the optometry device and an examinee.

As the detection unit, an imaging unit (for example, a camera including an imaging sensor, or the like) capable of detecting a contact between the optometry device and the examinee may be used in this case, the contact between the optometry device and the examinee may be determined by analyzing an image captured by the imaging unit.

Further, as the detection unit, a sensor (for example, at least one of an optical sensor, a pressure sensor, a load sensor, and the like) that can detect the contact between the optometry device and the examinee may be used. The detection unit may detect that the optometry device and the examinee are in contact with each other based on a detection signal generated when the optometry device and the examinee are in contact with each other. As an example, in a case where the detection unit is the load sensor, if the load sensor detects a load from the outside, the load sensor may convert the load into an electrical resistance value and output the value. The contact between the optometry device and the examinee may be detected based on presence or absence (in other words, presence or absence of an output of a detection signal) of an output of a potential resistance value. For example, the detection unit may detect that the optometry device and the examinee are in contact with each other when the potential resistance value is output.

When the optometry device has a forehead pad for bring into contact with a forehead of the examinee, the detection unit is provided in the forehead pad and may detect whether or not the forehead of the examinee is in contact with the forehead pad. The detection unit may detect that the forehead of the examinee is in contact with the forehead pad when the load is detected from the forehead pad. Further, for example, in a case where the optometry device has a jaw rest for placing a jaw of the examinee, the detection unit is provided in the jaw rest and may detect whether or not the jaw of the examinee is placed on the jaw rest. The detection unit may detect that the jaw of the examinee is in contact with the jaw rest when a load is detected from the jaw rest. Of course, in a case where the optometry device has both the forehead pad and the jaw rest, the detection unit may be provided in at least one of the forehead pad and the jaw rest.

In the present embodiment, the detection unit may not be configured to detect the contact between the optometry device and the examinee. The detection unit may be configured to detect a positional relationship between the optometry device and the examinee. As an example, the detection unit may be a distance sensor. Further, for example, the detection unit may be capture means. In this case, the capture means may imaging the optometry device and the examinee and detect whether or not the optometry device and the examinee are at a predetermined distance. Further, in this case, the imaging means may detect a face of the examinee by imaging the face of the examinee, <Determination Unit>

In the present embodiment, the optometry device includes a determination unit (for example, a control unit 107). The determination unit determines whether or not the subject eye can be examined. For example, a state where the subject eye can be examined is a state where examination of the subject eye can start. As an example, the face of the examinee may be fixed to the optometry device by using a forehead pad. For example, the face of the examinee may be fixed by using a jaw rest. Further, as an example, the optometric device and the examinee may be in a predetermined positional relationship.

The determination unit may determine whether or not the subject eye can be examined based on a detection result of the detection unit. For example, the determination unit may determine that examination of the subject eye is in a startable state when the detection unit detects the contact between the optometry device and the examinee. In more detail, the determination unit may determine that the examination of the subject eye can start when a detection signal is generated from the detection unit. Further, for example, the determination unit may determine that it is impossible to start the examination of the subject eye when the detection unit did not detect the contact between the optometry device and the examinee. In more detail, when the detection signal is not generated from the detection unit, it may be determined that the examination of the subject eye cannot start.

<Output Unit>

In the present embodiment, the optometry device includes a first output unit (for example, a control unit 303). The first output unit outputs determination information based on a determination result of the determination unit. According to this, the examiner can easily grasp whether or not the examinee can be examined.

The first output unit may output notification information for notifying the examiner of the determination result as the determination information. In this case, the notification information may be information (that is, information indicating that the examination of the subject eye can start or cannot start) indicating the determination result, information for guiding the examiner to a next operation, or the like.

The first output unit may output such notification information to a remote operation unit. For example, the first output unit may output the notification information as a message to a display unit included in the remote operation unit. Further, for example, the first output unit may output the notification information by generating a voice guide of the remote operation unit. Further, for example, the first Output unit may output the notification information by turning on or blinking a lamp in the remote operation unit.

Of course, the first output unit may output the notification information to a configuration element different from the remote operation unit. For example, the first output unit may output the notification information to a printer or the like for printing or may output the notification information to a memory, a server or the like for storage.

In the present embodiment, the optometry device includes a second output unit (for example, the control unit 107, the control unit 303). The second output unit outputs an instruction signal for instructing the next operation to at least one of the optometry device and the remote operation unit based on the determination result of the determination unit. Thereby, the examiner can efficiently examine the subject eye.

The second output unit may output an instruction signal to the optometry device. In this case, the instruction signal may be an instruction signal for causing the optometry device to start alignment, an instruction signal for causing the optometry device to start examination, and the like. The second output unit may output the instruction signal to the remote operation unit. In this case, the instruction signal may be an instruction signal for displaying a screen for setting the optometry device on the display unit provided in the remote operation unit.

In the present embodiment, the optometry device may be configured to serve as both the first output unit and the second output unit or may be configured to be provided separately. Further, in the present embodiment, the optometry device may be configured to perform either one of output of the determination information from the first output unit or output of the instruction signal from the second output unit or may be configured to perform both.

In the present embodiment, the optometry device may include an alignment unit. The alignment unit performs alignment between the subject eye and the optometry device. The alignment unit may have a configuration in which an alignment index is projected onto an anterior eye portion of the subject eye and alignment between the subject eye and the optometry device is performed by using an alignment index image.

In the present embodiment, the optometry device may include a fundus imaging unit. The fundus imaging unit images a fundus of the subject eye. For example, the fundus imaging unit may have a configuration of at least one of an ophthalmic optical coherence tomographic meter, a scanning laser ophthalmoscope, a fundus camera, and the like. Of course, the fundus imaging unit may have a configuration different from these configurations.

<Imaging Unit>

In the present embodiment, the optometry system includes an imaging unit (for example, an imaging unit 200). The imaging unit captures an image of an examination room including an examinee and the optometry device. For example, the examination room may be a bright room for examining a subject eye. As an example, the examination room may be a bright room for measuring optical characteristics of the subject eye. Further, for example, the examination room may be a dark room for examining the subject eye. As an example, the examination room may be a dark room for imaging an anterior eye portion or a fundus of the subject eye.

The imaging unit may image the examination room as a moving image. That is, the imaging unit may image the examination room in real time. Further, the imaging unit may image the examination room as a still image. In this case, the imaging unit may capture an image every predetermined time (for example, every 5 seconds).

The imaging unit may be capable of imaging an imaging portion room including the examinee and the optometry device under a clear vision. Further, the imaging unit may be capable of imaging an imaging portion room including the examinee and the optometry device under a night vision. In this case, a night vision camera may be used for the imaging unit. As an example of the night vision camera, a high-sensitivity camera that amplifies sensitivity to light, an infrared camera that detects infrared rays emitted from an object, and the like can be used.

Here, for example, in a field of ophthalmology, in order to reduce influence on an examination accuracy due to a change in ambient light such as a lighting apparatus in the examination room, a dark room is often made when examining the subject eye. By enabling imaging under the night vision as in the present embodiment, a state of the examinee can be observed even in a dark room, and the subject eye can be accurately examined.

The imaging unit may image the examination room such that a positional relationship (in other words, a layout between the examination room and the optometry device) between the examination room and the optometry device placed in the examination room can be grasped. For example, in this case, the imaging unit may be configured to look down on the examinee and the optometry device by being disposed at a position different from the optometry device. As an example, the imaging unit may be disposed in the examination room.

The imaging unit may be disposed at any position in the examination room as long as the examination room including the examinee and the optometry device can be imaged. For example, the imaging unit may be disposed in an upper portion of the examination room. According to this, the imaging unit easily images the entire examination room, and the examiner easily grasps a state of the examination room by using a captured image captured by the imaging unit.

The imaging unit may be disposed in a central portion in an upper portion of the examination room. In this case, an omnidirectional camera (360 degree camera) or the like may be used as the imaging unit. Further, the imaging unit may be disposed at a corner in an upper portion of the examination room. In this case, a directional camera, a camera having a swing function, or the like may be used as the imaging unit. Since the imaging unit is disposed in the upper portion and the corner of the examination room, the entire examination room is easily imaged even if a simple camera is used.

<Remote Operation Unit>

In the present embodiment, the optometry system includes a remote operation unit (for example, a remote operation unit 300). The remote operation unit may include an operation screen for operating the optometry device and a display unit (for example, a monitor 301) that displays the captured image captured by the imaging unit. Further, the remote operation unit may include a display control unit (for example, a control unit 303) that controls display on the display unit and causes the display unit to display an operation screen and the captured image. That is, the remote operation unit includes the display unit and the display control unit and enables the examiner to observe the captured image displayed on the display unit to guide the examinee to an examination position. With such a configuration of the optometry system, even if the examiner and the examinee are not in the same space, the examiner gives an appropriate instruction while observing the examinee to efficiently examine the subject eye.

The operation screen for operating the optometry device may be a screen used for examining the subject eye by using the optometry device. As an example, the operation screen may be a setting screen for performing various settings of the optometry device. In a case where the optometry device is an OCT device, a screen for setting a scanning position, a scanning pattern, and the like of measurement light for acquiring OCT data may be displayed as the setting screen. Further, as an example, the operation screen may be a result screen showing an examination result using the optometry device. In a case where the optometry device is the OCT device, a tomographic image generated from the OCT data may be displayed as the result screen. As an example, the operation screen may be a subject eye image obtained by imaging the subject eye. In a case where the optometry device is the OCT device, an anterior eye portion image captured by an anterior eye portion imaging optical system included in the OCT device may be displayed as a subject eye image.

The captured image captured by the imaging unit may be an image captured to guide the examinee to the optometry device. For example, the captured image may be an image obtained by imaging the entire examination room and may be an image in which the optometry device and the examinee can be observed. Further, for example, the captured image may be an image obtained by imaging at least a part of the examination room and may be an image in which the optometry device and the examinee can be observed.

An examination position where the examinee is guided may be a position of the optometry device. Further, the examination position where the examinee is guided may be a position spaced apart from the optometry device. As an example, the examination position where the examinee is guided may be a position of a chair used together with the optometry device, or the like.

<Display Control Unit>

In the present embodiment, the display control unit included in the remote operation unit controls display on the display unit to display an operation screen on the display unit. Further, in the present embodiment, the display control unit included in the remote operation unit controls display on the display unit and causes the display unit to display the captured image captured by the imaging unit. For example, the display control unit may control the display of the display unit based on at least one of an operation signal manually input by the examiner, an operation signal automatically generated based on an operation of the optometry device, and the like.

The display control unit may control the display of the display unit such that the operation screen and the captured image are displayed on the same screen of the display unit. In this case, the display control unit may display the operation screen and the captured image on the screen of the display unit at the same timing. In this case, the display control unit may display the operation screen and the captured image on the screen of the display unit at different timings. For example, the display control unit may be configured to first display either one of the operation screen and the captured image on the display unit and the other on the display unit later.

For example, as the operation screen and the captured image are displayed on the same screen, even if the examiner is not in the same space as the examinee, the examiner can observe a series of operations of the examinee (for example, operations from when the examinee enters the examination room until the subject eye can be examined by using the optometry device, and the like) and states (for example, a state during examination of the subject eye, and the like) of the examinee while operating the optometry device, and the subject eye can be examined efficiently.

In the present embodiment, the remote operation unit may include a signal acquisition unit (for example, the control unit 303). For example, the signal acquisition unit acquires a switching signal for switching between the operation screen and the captured image. The switching signal may be manually generated by an operation of the examiner. Further, the switching signal may be automatically generated at a preset timing. As an example, the switching signal may be generated at a timing when the determination unit determines that the subject eye is in an examinable state. In more detail, the switching signal may be generated at the timing when a forehead of the examinee comes into contact with the forehead pad, the timing when a jaw of the examinee is placed on the jaw rest, and the like.

In a case where the remote operation unit is configured to include such a signal acquisition unit, the display control unit may control display on the display unit based on the switching signal such that the operation screen and the captured image are switched to be displayed on the screen of the display unit. For example, the display control unit may control the display of the display unit based on the switching signal such that either the operation screen or the captured image is displayed on the screen of the display unit. Further, for example, the display control unit may control the display of the display unit based on the switching signal such that either the operation screen or the captured image is removed from a state where both the operation screen and the captured image are displayed on the same screen of the display unit. Further, for example, the display control unit control the display of the display unit based on the switching signal such that both the operation screen and the captured image are displayed on the same screen of the display unit by adding the other from a state where either one of the operation screen and the captured image is displayed on the screen of the display unit.

For example, by switching and displaying the operation screen and the captured image on the screen, the examiner can easily give an instruction to the examinee or examine the subject eye while observing a screen where the operation screen and the captured image are switched manually or automatically.

<Assignment of Operation to Operation Unit Operating Optometry Device>

In the present embodiment, the optometry system includes a first operation unit (for example, an operation unit 101 and a monitor 106). The first operation unit is provided in a housing of the optometry device or near the optometry device and operates the optometry device. For example, in the present embodiment, the first operation unit may be provided in the housing of the optometry device. A user interface such as a mouse, a joystick, a keyboard, a tablet terminal, or a controller may be used as the first operation unit.

In the present embodiment, the optometry system includes a second operation unit (for example, an operation unit 302). The second operation unit is provided spaced apart from the optometry device and operates the optometry device. For example, in the present embodiment, the second operation unit may be provided in the remote operation unit. The user interface such as the mouse, the joystick, the keyboard, the tablet terminal, or the controller may be used as the second operation unit.

<Setting Unit>

In the present embodiment, the optometry system includes a first setting unit (for example, a control unit 107). The first setting unit assigns a first operation of the optometry device to a first operation signal input from the first operation unit. The first setting unit may be configured to assign one operation to the first operation unit or may be configured to assign a plurality of operations.

Further, in the present embodiment, the optometry system includes a second setting unit (for example, the control unit 107). The second setting unit assigns a second operation of the optometry device to a second operation signal input from the second operation unit. The second setting unit may be configured to assign one operation to the second operation unit or may be configured to assign a plurality of operations.

That is, in the present embodiment, the first setting unit and the second setting unit can appropriately assign operations to the first operation unit and the second operation unit. In other words, the operations for the first operation unit and the second operation unit can be appropriately set by the first setting unit and the second setting unit.

A first operation and a second operation are at least one of operations performed when examining the subject eye by using the optometry device. As an example, at least one of an alignment operation for aligning the optometry device and the subject eye, an imaging operation for imaging the subject eye, a setting operation for setting an examination condition for examining the subject eye, an examination start operation for starting examination of the subject eye, an adjustment operation for adjusting a height of a jaw rest, an adjustment operation for adjusting a position of the forehead pad, and the like can be used. Of course, the first operation and the second operation may be other operations. For example, the first operation and the second operation may be operations relating to the examination of the subject eye using the optometry device from the alignment between the optometry device and the subject eye.

The first setting unit and the second setting unit may be set such that at least a part of the same operation of the optometry device is assigned to each of the first operation unit and the second operation unit. In this case, the first operation and the second operation may all be the same. As an example, the alignment operation and the adjustment operation may be assigned to the first operation unit, and the alignment operation and the adjustment operation may be assigned to the second operation unit. Further, in this case, the first operation and the second operation may partially overlap. As an example, the alignment operation and an imaging operation may be assigned to the first operation unit, and the alignment operation and the adjustment operation may be assigned to the second operation unit.

Further, the first setting unit and the second setting unit may be set so as to assign different operations of the optometry device to the first operation unit and the second operation unit, respectively. That is, the first operation and the second operation may be different. As an example, an examination start operation may be assigned to the first operation unit, and the alignment operation may be assigned to the second operation unit.

In the above description, a case where the first setting unit and the second setting unit may be set to assign a predetermined operation to each of the first operation unit and the second operation unit is exemplified, but the present disclosure is not limited to this. The first setting unit and the second setting unit may be set such that an operation obtained by subdividing a predetermined operation is assigned to each of the first operation unit and the second operation unit. As an example, the first setting unit may be set so as to assign movement operations in the horizontal and vertical directions of the alignment operation to the first operation unit, and the second setting unit may be set so as to assign a movement operation in the front-rear direction of the alignment operation is assigned to the second operation unit.

For example, in the optometry system according to the present embodiment, since the examiner operates the optometry device from a separated location, it is difficult to know a sense of distance in the front-rear direction in the alignment operation. By assigning an operation for each movement direction of the alignment operation to the first operation unit and the second operation unit, it is possible to reduce a possibility that the examinee and the optometry device are in contact with each other.

For example, assignments of the first operation and the second operation by the first setting unit and the second setting unit may be previously set. The setting may be automatically changed by acquiring operator information (will be described below). Of course, the examiner may randomly change the setting.

For example, as such, by configuring the operation of the optometry device using the first operation unit and the second operation unit, it is possible to assign an appropriate operation according to a location or skill of an operator (that is, an examiner, an examinee, an assistant or the like) who operates the optometry device, content of the operation when examining the subject eye, and the like. Even if the examiner is not in a space where the optometry device is disposed, the examiner can easily examine the subject eye.

In the present embodiment, in a case where the optometry device includes the above-described fundus imaging unit, at least one of the first setting unit and the second setting unit may assign an operation (in other words, an imaging start operation) for starting imaging by the fundus imaging unit to operation signals input from the first operation unit and the second operation unit. As an example, in the present embodiment, it may be set such that the imaging start operation is assigned to the operation unit operated by the examiner and the imaging start operation is not assigned to the operation unit operated by the examinee. Accordingly, even if an operation signal of imaging start is generated by the examinee, an abnormal operation of the optometry device is suppressed.

Further, in the present embodiment, in a case where the optometry device includes the above-described alignment unit, at least one of the first setting unit and the second setting unit may assign an operation (in other words, an alignment operation) for performing alignment by the alignment unit to operation signals input from the first operation unit and the second operation unit. As an example, in the present embodiment, it may be set such that the alignment operation is not assigned to the operation unit operated by the examiner and the alignment operation is assigned to the operation unit operated by the examinee. As the examinee who can grasp the sense of distance between the subject eye and a device performs the alignment operation, it is possible to perform the alignment safely.

<Operation Control Unit>

In the present embodiment, the optometry system includes an operation control unit (for example, the control unit 107). The operation control unit prohibits performing of an operation of the Optometry device by the other operation signal when an operation of the optometry device is performed by either one of the first operation signal and the second operation signal.

For example, the operation control unit may be configured to prohibit the operation of the optometry device from being performed by prohibiting the other operation signal from being input when the operation of the optometry device is being performed by one of the first operation signal and the second operation signal. Further, for example, the operation control unit may be configured to prohibit the operation of the optometry device from being performed by prohibiting the other operation signal from transmitting or receiving when the operation of the optometry device is being performed by either one of the first operation signal and the second operation signal. Further, for example, the operation control unit may be configured to prohibit the operation of the optometry device from being performed by prohibiting the other operation signal from operating when the operation of the optometry device is performed by one of the first operation signal and the second operation signal.

In the present embodiment, as the first setting unit and the second setting unit do not assign a predetermined operation to either the first operation unit or the second operation unit, a configuration may be used in which the operation of the optometry device is prohibited from being performed.

Such an operation control unit suppresses switching to a control operation based on the other operation signal while a control operation based on one operation signal is being performed, and it is possible to perform examination of a subject eye efficiently and safely.

An operator who operates the optometry device may be notified of whether or not the optometry device is in a state where an operation thereof can be performed or whether or not the optometry device is in a state where an operation thereof is prohibited. For example, the notification may be made by at least any one of display on a display unit, a voice guide, and the like.

<Operator Information Acquisition Unit>

In the present embodiment, the optometry system includes an information acquisition unit (for example, the control unit 303). The information acquisition unit acquires operator information that is information of an operator who operates the optometry device. The operator information may be information relating to an operator (for example, an examiner, an assistant, or the like). An example includes a face, a name, an affiliation, a history, and the like of the operator. The face of the operator may be acquired as an image (a moving image or a still image) obtained by imaging the operator. For example, the optometry system may be provided with capture means for imaging the operator.

The information acquisition unit may acquire the operator information input by the operator. Further, the information acquisition unit may acquire the operator information by calling a corresponding operator information from a server in which the operator information is stored. In this case, the operator information may be acquired by inputting a user ID, reading a one-dimensional code (for example, a barcode) or a two-dimensional code (for example, a QR code (registered trademark)), and the like.

For example, the operator information acquired by the information acquisition unit may be controlled by a display control unit (for example, the control unit 107) to be displayed on a screen of the display unit. The display unit may be provided in the housing of the optometry device or near the optometry device and the operator information may be displayed on a monitor or the like observed by the examinee. According to this, even if the examiner and the examinee are not in the same space, the examinee can know information of the examiner and can take the examination with peace of mind.

The present disclosure is not limited to the optometry system described in the present embodiment. For example, terminal control software (program) that performs functions of the above-described embodiments is supplied to the optometry system or the optometry device via a network or various storage media, and the control unit (for example, CPU) of the optometry system or the optometry device can also read and execute the program.

Example

An example of an optometry system according to the present example will be described with reference to the drawings.

FIG. 1 is a schematic diagram of an optometry system 1. The optometry system 1 is an optometry system for examining a subject eye of an examinee. The optometry system 1 includes an optometry device 100, an imaging unit 200, a remote operation unit 300, and the like. The optometry device 100, the imaging unit 200, and the remote operation unit 300 include a communication unit (not illustrated) and are connected to each other via a wired or wireless network.

In the optometry system 1 of the present example, the optometry device 100, the imaging unit 200, and the remote operation unit 300 may be connected via a shared server 400. In this case, the shared server may include a control unit 401 and a storage unit (memory) 402.

The memory 402 may be a non-transitory storage medium that can hold stored contents even when power supply is interrupted. For example, a hard disk drive, a flash ROM, a USB memory, and the like can be used. The memory 402 may store various types of information relating to examination of a subject eye E in the OCT device 100, an acquired anterior eye portion image, acquired OCT data, and the like. Further, the memory 402 may store a captured image, a voice, and the like by the imaging unit 200.

FIG. 2 illustrates a use example of the optometry system 1. For example, the optometry device 100 and the imaging unit 200 included in the optometry system 1 may be installed in an examination room 10 where an examinee P is present. Further, for example, the remote operation unit 300 included in the optometry system 1 may be installed in the operation room 20 where the examiner D is present.

<Optometry Device>

The optometry device 100 is used for examining the subject eye F of the examinee P. In the present example, an eye imaging device is illustrated as the optometry device 100. The eye imaging device may be an OCT device having a configuration of a so-called ophthalmic optical coherence tomography for an eye. Hereinafter, the optometry device 100 will be referred to as the OCT device 100.

The OCT device 100 includes an OCT optical system that detects an interference signal by measurement light and reference light applied to the subject eye F and acquires OCT data of the subject eye E by processing the interference signal. The OCT device 100 includes an operation unit (joystick) 101, a movement table 102, a measurement unit 103, a face support unit 104, a monitor 106, a control unit 107, and the like.

The operation unit 101 relatively moves the measurement unit 103 in a vertical direction (Y direction), a horizontal direction (X direction), and a front-rear direction (Z direction) for the subject eye E. By operating the operation unit 101, an X moving mechanism (not illustrated) and a Z moving mechanism (not illustrated) provided on the movement table 102 are driven, and the measurement unit 103 disposed in an upper portion of the movement table 102 moves in the horizontal direction and the front-rear direction. Further, by operating the operation unit 101, a Y moving mechanism (not illustrated) provided in the measurement unit 103 is driven, and the measurement unit 103 moves in the vertical direction.

An anterior eye portion imaging optical system (not illustrated), an OCT optical system (not illustrated), and the like are contained inside the measurement unit 103. The anterior eye portion imaging optical system images an anterior eye portion of the subject eye E. The anterior eye portion imaging optical system may be configured to include a light source that illuminates an anterior eye portion, an image sensor that images the anterior eye portion, and the like. Of course, the anterior eye portion imaging optical system may have a configuration different from this. The OCT optical system may be configured to include a light source that emits low-coherent light, a light splitter that divides light emitted from the light source into the measurement light and the reference light, a measurement optical system that guides the measurement light to the subject eye E, a scanning unit that scans measurement light in a transverse direction on a fundus of the subject eye E; a reference optical system that generates the reference light, a detector that detects an interference signal generated by combining the measurement light and the reference light, and the like. Of course, the OCT optical system may have a configuration different from these.

The face support unit 104 supports a face of the examinee P. The face support unit 104 includes a forehead pad 104a and a jaw rest 104b. A forehead of the examinee P is brought into contact with the forehead pad 104a. A jaw of the examinee P is placed on the jaw rest 104b. A detector 105 is provided on the jaw rest 104b. The detector 105 detects whether or not the jaw of the examinee P is placed on the jaw rest 104b. The detector 105 may be configured by at least one of an optical sensor, a pressure sensor, a load sensor, and the like. For example, in the present example, the load sensor is used as the detector 105, and a load due to the jaw of the examinee P being placed on the jaw rest 104b is detected by the load sensor. A detection result of the detector 105 is output to the control unit 107.

Figure 3:
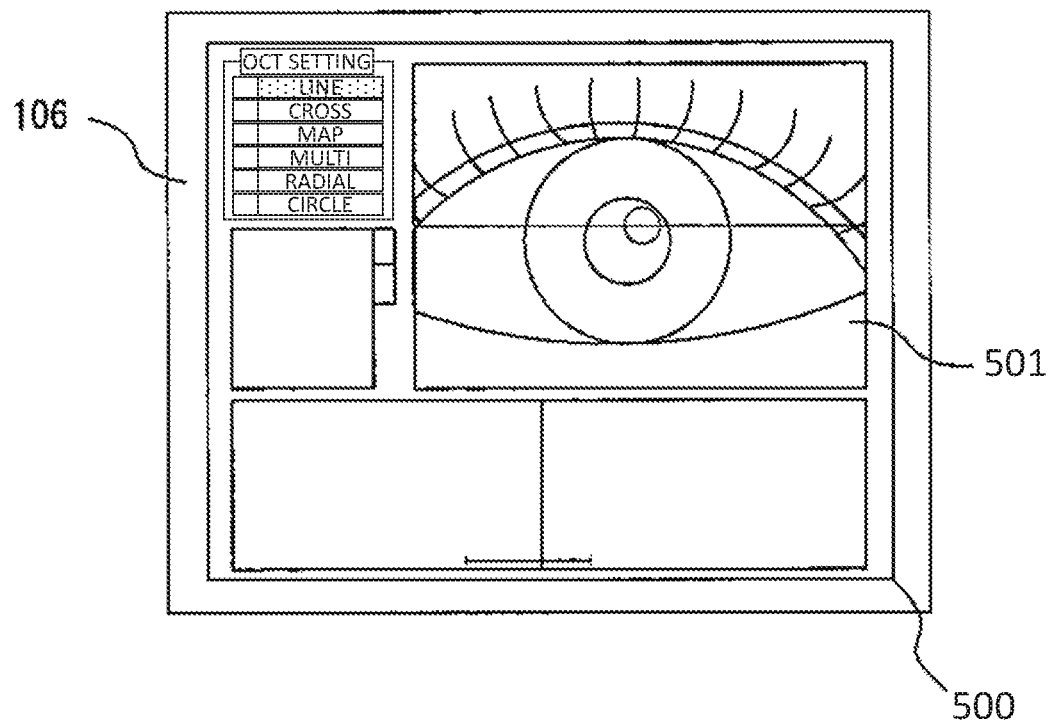
FIG. 3 is an example of a screen of a monitor in an OCT device.

FIG. 3 is an example of a screen of the monitor 106 in the OCT device 100. An operation screen 500 for operating the optometry device 100 is displayed on the monitor 106. The operation screen 500 may be at least one of a setting screen (for example, setting screen for setting a scanning position of the measurement light, a scanning pattern, a region in a depth direction, and the like) for obtaining OCT data by the OCT optical system, and a tomographic image generated from the OCT data, an anterior eye portion image captured by the anterior eye portion imaging optical system, and the like. For example, FIG. 3 illustrates an anterior eye portion image 501 as the operation screen 500, In the present example, the operation screen 500 is displayed on the monitor 106 of the OCT device 100 and is also displayed on a monitor 301 of the remote operation unit 300.

The monitor 106 may be a touch panel, or the monitor 106 may also serve as an operation unit. In this case, an operation signal corresponding to an operation of the examinee P (or an assistant which will be described below) is input from the monitor 106 and output to the control unit 107.

The control unit 107 includes a general CPU (Central Processing Unit), a RAM, a ROM, and the like. The CPU controls the optometry device 100. The RAM temporarily stores various types of information. The ROM stores a program for controlling the operation of the optometry device 100, and the like. The control unit 107 is electrically connected to an operation unit 101, a drive unit of a moving mechanism (an X moving mechanism, a Y moving mechanism, and a Z moving mechanism) not illustrated, the detector 105, the monitor 106, a light source or a detector included in the OCT optical system, a light source or an imaging element included in the anterior eye portion imaging optical system, and the like.

<Imaging Unit>

The imaging unit 200 is used for imaging an examination room 10. The imaging unit 200 may image the examination room 10 as a moving image or may image as a still image for each regular time. The imaging unit 200 may be disposed at any position of the examination room 10 as long as the examination room 10 including the examinee P and the optometry device 100 can be imaged. That is, the imaging unit 200 may be disposed in the examination room 10 at an angle of view including at least the examinee P and the optometry device 100. In the present example, the imaging unit 200 is disposed at a corner and an upper portion of the examination room 10.

The imaging unit 200 includes a detector 201, a control unit 202, and the like. The detector 201 may be an imaging sensor such as a CCD (Charge Coupled Device) or a CMOS (Complementary Metal Oxide Semiconductor).

The control unit 202 includes a general CPU, a RAM, a ROM, and the like and may control the imaging unit 200 to zoom an image captured by the imaging unit 200 or pan and tilt the imaging unit 200 by using a rotation mechanism not illustrated or temporarily store the captured image and voice. The detector 201 is electrically connected to the control unit 202, In the present example, a night vision camera (for example, a high sensitivity camera, an infrared camera, or the like) that can be used even under night vision may be used as the imaging unit 200. Thereby, the examination room 10 can be imaged under the night vision, In the present example, the imaging unit 200 may include a microphone and a speaker not illustrated. For example, a voice of the examinee P in which the microphone of the imaging unit 200 is mounted may be output from the speaker (not illustrated) of the remote operation unit 300 and transferred to an examiner D. Further, for example, the voice of the examiner D in which the microphone (not shown) of the remote operation unit 300 is mounted may be output from the speaker (not illustrated) of the imaging unit 200 and transferred to the examinee P.

<Remote Operation Unit>

The remote operation unit 300 guides the examinee P to the optometry device 100 and is used to set a state in which the subject eye E can be examined by the optometry device 100 (in other words, a state in which examination of the subject eye E can be started). For example, in the present example, as the examinee P places his jaw on the jaw rest 104b, the subject eye E can be examined by the optometry device 100. The remote operation unit 300 includes a monitor 301, an operation unit (mouse) 302, a control unit 303, and the like.

Figure 4:
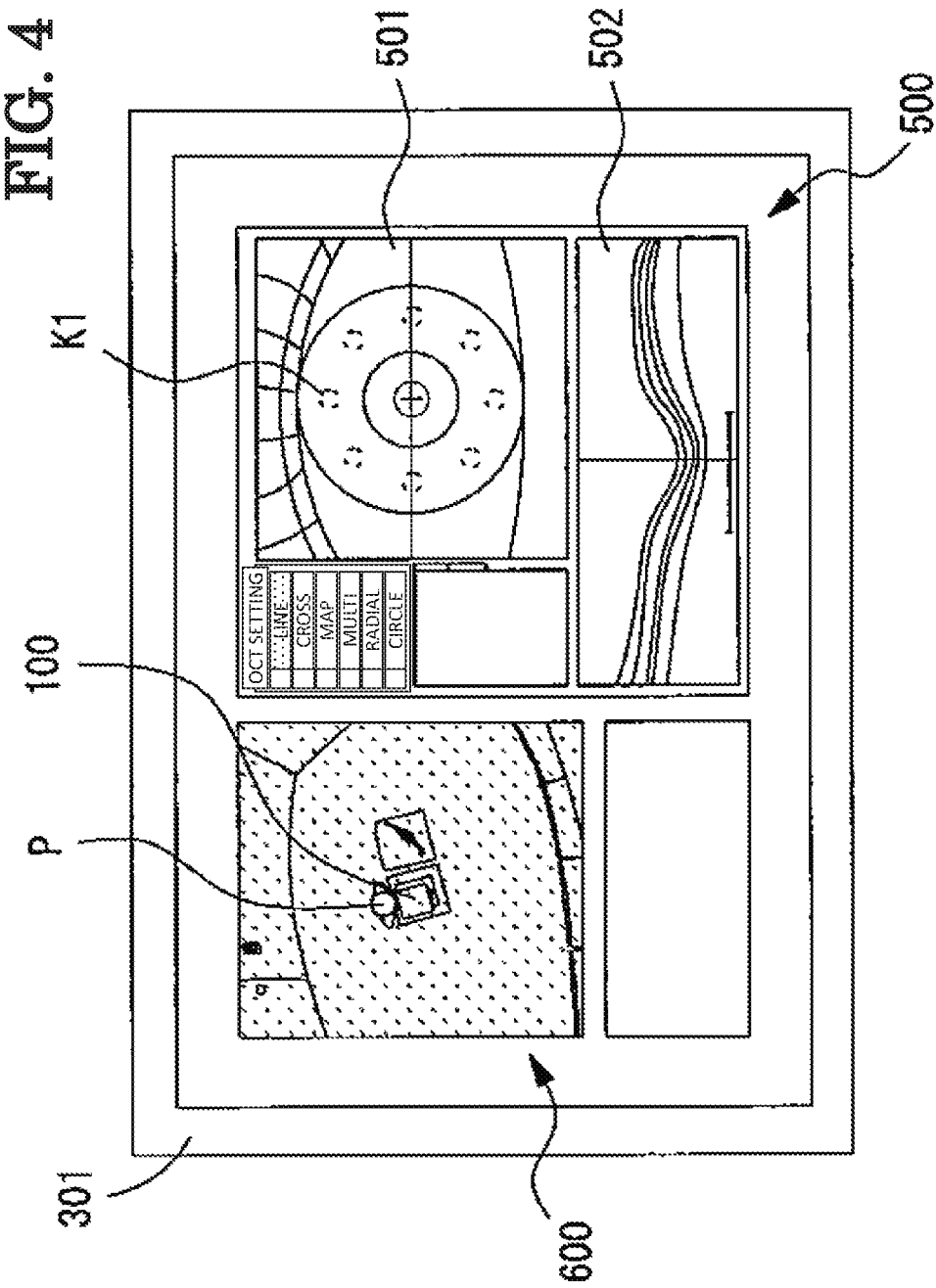
FIG. 4 is an example of a screen of a monitor in a remote operation unit.

FIG. 4 is an example of a screen of the monitor 301 in the remote operation unit 300. An operation screen 500 for operating the optometry device 100 is displayed on the monitor 301. For example, in FIG. 4, the above-described anterior eye portion image 501 and a tomographic image 502 generated from the OCT data are displayed as the operation screen 500. Further, the monitor 301 displays the captured image 600 captured by the imaging unit 200. The captured image 600 shows the examinee P, the OCT device 100, and the like.

In the present example, an example using one monitor 301 is given, hut a plurality of monitors may be used. As an example, two monitors may be used as a first monitor and a second monitor, and either the operation screen 500 or the captured image 600 may be displayed on the first monitor, and the other may be displayed on the second monitor. That is, a screen of the monitor 301 may be expanded by using a plurality of monitors.

Further, the monitor 301 may be a touch panel, and the monitor 301 may also serve as the operation unit 302. In this case, an operation signal corresponding to an operation of the examiner D is input from the monitor 301 and output to the control unit 303.

The operation signal corresponding to the operation of the examiner D is input from the operation unit 302. The operation signal input from the operation unit 302 is output to the control unit 303. Furthermore, this operation signal is output from the control unit 303 to the control unit 107 of the OCT device 100 via the shared server 400.

The control unit 303 includes a general CPU, a RAM, a ROM, and the like, and controls the remote operation unit 300 to control display of the monitor 301. The monitor 301, the operation unit 302, and the like are electrically connected to the control unit 303.

In the present example, the control unit 303 controls the monitor 301 to simultaneously display the operation screen 500 and the captured image 600 on the screen of the monitor 301. Simultaneously displaying the operation screen 500 and the captured image 600 is not limited necessarily to displaying the operation screen 500 and the captured image 600 at the same timing. Both the operation screen 500 and the captured image 600 may be set to a state of being displayed on the screen of the monitor 301, and the operation screen 500 and the captured image 600 may be displayed at different timings.

As an example, the control unit 303 may display the operation screen 500 and the captured image 600 on the screen of the monitor 301, based on each of an operation signal (first operation signal) for displaying the operation screen 500 and an operation signal (second operation signal) for displaying the captured image 600. For example, based on these operation signals, one of the operation screen 500 and the captured image 600 may be first displayed on the screen of the monitor 301, and the other may be displayed on the screen of the monitor 301 later. That is, the operation screen 500 and the captured image 600 may be displayed at different timings. The first operation signal and the second operation signal may be used together, and the operation screen 500 and the captured image 600 may be displayed at the same timing based on the output of the first operation signal (second operation signal).

<Assignment of Operation>

The optometry system 1 can assigns an input of the operation signals for the OCT device 100 to perform various operations to each of the operation unit 101 included in the OCT device 100 and the operation unit 302 included in the remote operation unit 300. For example, the operation of the OCT device 100 may be an operation for performing alignment of the OCT device 100 and the subject eye F, setting for acquiring the OCT data, start of examination, a height adjustment of the jaw rest 104h, and the like (details will be described later).

The operation assignment in the OCT device 100 may be set previously for each operation of the OCT device 100. The operation assignment may be randomly settable by the examiner D. The setting may be automatically changed according to operator information of an operator (for example, THE examiner D) who operates the OCT device 100.

<Display of Operator Information>

The optometry system 1 can acquire operator information indicating an operator (for example, the examiner Di who operates the OCT device 100 and can present the operator information to the examinee P. For example, the operator information may be acquired by inputting a user ID, reading a one-dimensional code (for example, a barcode) or a two-dimensional code (for example, a QR code (registered trademark)), and the like.

<Operation>

An operation for the examiner D in the operation room 20 to guide the examinee P who entered the examination room 10 to the OCT device 100 by using the optometry system having the above-described configuration, and an operation of examining the subject eye E by using the OCT device 100 will be described.

<Turn-on of Power of OCT Device>

First, the examiner D turns on power of the OCT device 100. For example, the examiner D operates the operation unit 302 to select a power switch (not illustrated) for turning on the power of the OCT device 100 displayed on the monitor 301. The control unit 303 of the remote operation unit 300 transmits an operation signal input from the power switch to the control unit 107 of the OCT device 100 via the shared server 400. The control unit 107 of the OCT device 100 activates the OCT device 100 in response to the received operation signal. If the OCT device 100 is activated, a completion signal indicating that the OCT device 100 is activated is issued.

<Display of Operation Screen on Remote Operation Unit>

The control unit 107 of the OCT device 100 transmits the operation screen 500 for operating the OCT device 100 to the control unit 303 of the remote operation unit 300 in response to the completion signal. The control unit 303 displays the received operation screen 500 on the monitor 301.

<Assignment of Operation of OCT Device>

The examiner D previously assigns an input of an operation signal by which the OCT device 100 performs various operations to each of the operation unit 302 operated by the examiner D and the operation unit 101 operated by the examinee P. The examiner D operates the operation screen 500 displayed on the monitor 301 to call an operation setting screen 503 for setting the operation assignment of the OCT device 100.

Figure 5:
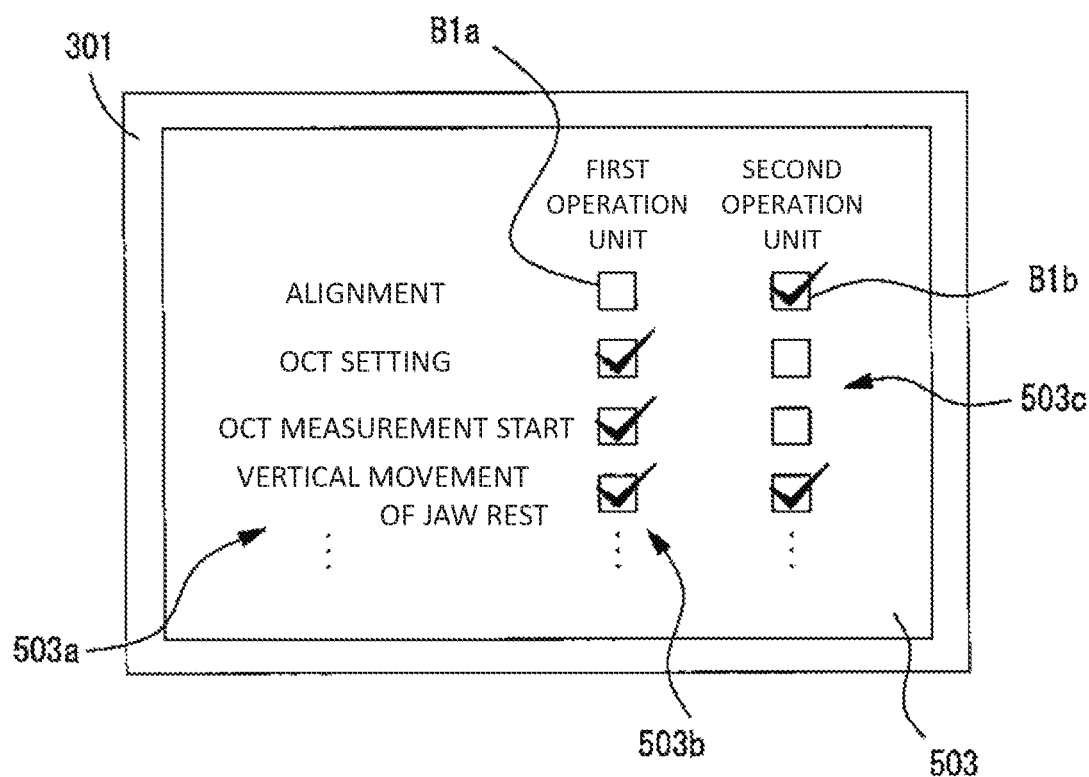
FIG. 5 is an example of an operation setting screen.

FIG. 5 is an example of the operation setting screen 503. The operation setting screen 503 displays a list 503a of operations of the OCT device 100, boxes 503b for selecting an operation assigned to the operation unit 302 (displayed as the first operation unit in FIG. 5) operated by the examiner D, and boxes 503c for selecting an operation assigned to the operation unit 101 (displayed as the second operation unit in FIG. 5) operated by examinee P.

The examiner D changes whether to input the operation signal from the operation unit 302 or to input the operation signal from the operation unit 101 or to input the operation signal from the operation unit 302 and the operation unit 101, for various operations of the OCT device 100. That is, whether performing the various operations is instructed by the examiner D or the examinee P or both the examiner D and the examinee P is selected for the OCT device 100, For example, the assignment will be described by taking an alignment operation for performing alignment of the OCT device 100 and the subject eye E as an example.

In this example, since the examiner D is in the operation room 20 and the examinee P is in the examination room 10, the examiner D observes the operation screen 500 (for example, the anterior eye portion image 501) and the captured image 600 displayed on the monitor 301, thereby, indirectly confirming the subject eye E of the examinee P. In the alignment of the OCT device 100 and the subject eye E, it is necessary to move the measurement unit 103 in the vertical direction, the horizontal direction, and the front-rear direction for the subject eye E. However, since the examiner D sees the subject eye E beyond the monitor 301, it is difficult to grasp a positional relationship between the subject eye E and the measurement unit 103. Particularly, it is difficult to grasp a positional relationship (in other words, a sense of distance between the subject eye E and the measurement unit 103) between the subject eye E and the measurement unit 103 in the front-rear direction.

Therefore, since the examiner D assigns an input of the operation signal for performing the alignment operation to the operation unit 101 operated by the examinee P, the examinee P may be set to be able to instruct performing of the alignment operation. The examiner D selects a box B1b corresponding to the alignment operation among the boxes 503c for selecting an operation assigned to the operation unit 101 (second operation unit) on the operation setting screen 503.

The control unit 303 of the remote operation unit 300 transmits the selection signal issued when the box B1b is selected to the control unit 107 of the OCT device 100 via the shared server 400. The control unit 107 of the OCT device 100 permits the operation unit 101 to input an operation signal for performing the alignment operation in response to the received selection signal.

For example, by doing so, the alignment operation for performing alignment of the OCT device 100 and the subject eye E may be assigned only to the operation unit 101. That is, only the examinee P may be set to be able to instruct performing of the alignment operation.

In the present example, the examiner D may select the box B1a corresponding to the alignment operation among the boxes 503b for selecting the operation assigned to the operation unit 302 (first operation unit). In this case, since the selection signal due to the selection of the box B1a is not issued, the control unit 303 of the remote operation unit 300 prohibits an input of the operation signal for performing the alignment operation by the operation unit 302.

Of course, the examiner D is not limited to the alignment operation and may set each of an operation (setting operation) of performing setting for obtaining OCT data by the OCT device 100, an operation (examination start operation) for starting an examination using the OCT device 100, an operation (imaging operation) for imaging a subject eye, an operation (jaw rest adjustment operation) for adjusting a height of the jaw rest 104b, and the like so as to be assigned to at least one of the operation unit 302 and the operation unit 101.

For example, in the present example, the setting operation and the examination start operation are assigned only to the operation unit 302. That is, performing the setting operation and the examination start operation is set such that only the examiner D can instruct. Further, for example, in the present example, the jaw rest adjustment operation is assigned to the operation unit 302 and the operation unit 101. That is, performing the jaw rest adjustment operation is set such that the examiner D and the examinee P can instruct.

<Turn-on of Power of Imaging Unit>

If assigning the operation of the OCT device 100 ends, the examiner D turns on power of the imaging unit 200. For example, the examiner D operates the operation unit 302 to select a power switch (not illustrated) for turning on the power of the imaging unit 200 displayed on the monitor 301. The control unit 303 of the remote operation unit 300 transmits an operation signal input from the power switch to the control unit 202 of the imaging unit 200 via the shared server 400. The control unit 202 of the imaging unit 200 activates the imaging unit 200 in response to the received operation signal. If the imaging unit 200 is activated, a completion signal indicating that the imaging unit 200 is activated is issued.

<Display of Captured Image on Remote Operation Unit>

The control unit 202 of the imaging unit 200 starts imaging of the examination room 10 in response to the completion signal. The control unit 202 of the imaging unit 200 transmits the captured image 600 sequentially captured by the detector 201 to the control unit 303 of the remote operation unit 300. The control unit 303 displays the received captured image 600 on the monitor 301.

For example, the operation screen 500 of the OCT device 100 and the captured image 600 of the examination room 10 captured by the imaging unit 200 are simultaneously displayed on the monitor 301 observed by the examiner D by doing so. That is, the operation screen 500 and the captured image 600 are displayed on the same screen on the monitor 301.

<Guide of Examinee>

When the examiner D observes the captured image 600 displayed on the monitor 301 and confirms that the examinee P has entered the examination room 10, the examiner D instructs the examinee P to sit in front of the OCT device 100. Further, if the examiner D confirms that the examinee P is sit in front of the OCT device 100, the examiner D instructs the examinee P to place his or her jaw on the jaw rest 104b of the OCT device 100.

A detector 105 is provided on the jaw rest 104h of the OCT device 100. When detecting an external load, the detector 105 detects that a jaw of the examinee P is placed on the jaw rest 104b. Further, the detector 105 converts the load into an electrical signal and outputs the electrical signal to the control unit 107.

If the electrical signal is input, the control unit 107 determines that a jaw of the examinee P is placed on the jaw rest 104b and the subject eye E is in an examinable state. Further, the control unit 107 transmits a determination result indicating that the subject eye E is in the examinable state to the control unit 303 of the remote operation unit 300 via the shared server 400. The control unit 303 of the remote operation unit 300 may display a message M1 (see FIG. 6) on the monitor 301 based on a detection result of the detector 105. For example, in the present example, if it is detected that the subject eye E is in the examinable state, a message for notifying that the examiner D can start a next operation is displayed.

If the examiner D guides the examinee P to the OCT device 100 and confirms that the subject eye is in the examinable state, the examiner D selects a power switch (not illustrated) displayed on the monitor 301 to interrupt electricity of the examination room 10. In the present example, since the imaging unit 200 is a night vision camera, the captured image 600 is captured under night vision even if the electricity of the examination room 10 is interrupted, and states of the examination room 10 and the examinee P can be observed on the monitor 301.

<Alignment of Subject Eye>

The examiner D observes the captured image 600 displayed on the monitor 301 and instructs the examinee P to watch the monitor (not illustrated) included in the measurement unit 103. For example, contents of the instruction of the examiner D gives to the examinee P may be displayed as a message on the monitor (not illustrated). Further, for example, a fixation target for fixing the subject eye may be displayed on the monitor (not illustrated). For example, after such a message is displayed for a certain period of time, the message may be automatically switched to the fixation target. Of course, the message and the fixation target may be displayed simultaneously.

Further, the examiner D observes the captured image 600 displayed on the monitor 301 and instructs the examinee P to start alignment. For example, the examiner D may instruct the examinee P to operate an alignment start switch (not illustrated) provided in the operation unit 101 of the OCT device 100. If the examinee P operates the alignment start switch, the control unit 107 controls an anterior eye portion imaging optical system in response to a start signal from the alignment start switch to capture the anterior eye portion image 501 of the subject eye E and to project an alignment index image K1 onto a cornea of the subject eye E. Further, the control unit 107 uses the alignment index image K1 to detect a positional shift of a corneal apex position (substantially corneal apex position) of the subject eye E for a measurement optical axis of the measurement unit 103 and to perform an automatic alignment.

Figure 6:
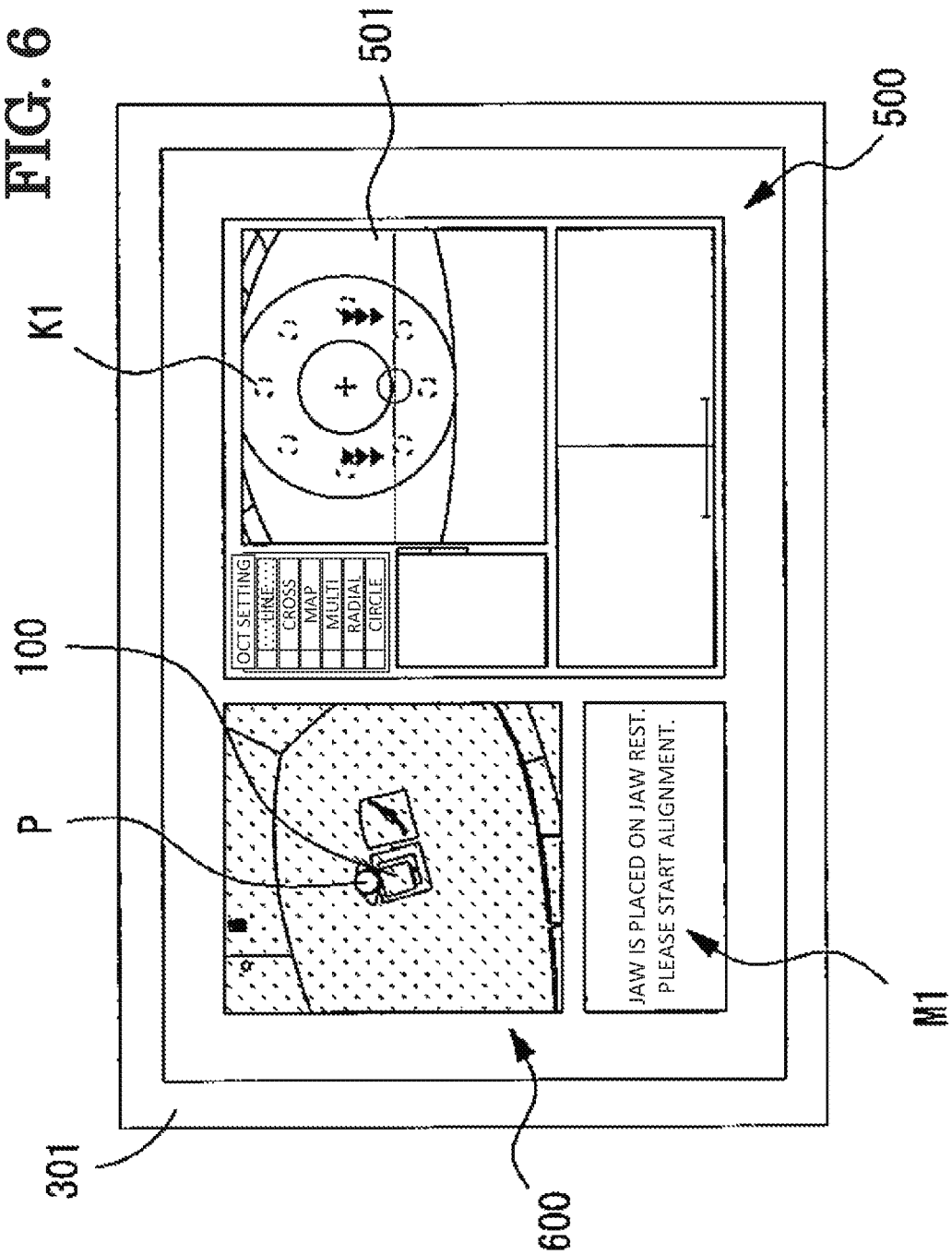
FIG. 6 is another example of the screen of the monitor in the remote operation unit.

FIG. 6 is an example of a screen of the monitor 301. The control unit 107 of the OCT device 100 transmits the anterior eye portion image 501 to the control unit 303 of the remote operation unit 300 via the shared server 400, and the control unit 303 causes the monitor 301 to display the anterior eye portion image 501. That is, the anterior eye portion image 501 of the subject eye E is displayed on the monitor 301 as the operation screen 500 of the OCT device 100. The examiner D can confirm alignment states of the OCT device 100 and the subject eye E by observing the anterior eye portion image 501 displayed on the monitor 301.

In the present example, the alignment operation of the OCT device 100 is not assigned to the operation unit 302 operated by the examiner D. Accordingly, even if the examiner D operates the operation unit 302, an operation signal for performing the alignment operation is not input. At this time, a message indicating that an operation from the operation unit 302 cannot be performed may be displayed on the monitor 301 observed by the examiner D.

Of course, when the alignment operation is assigned to the operation unit 302 operated by the examiner D in addition to the operation unit 101 operated by the examinee P, and the alignment by the examinee P is not successful, the examiner D may be able to perform alignment.

<Adjustment of Jaw Rest>

In the automatic alignment described above, when the subject eye E is shifted to a position higher or lower than a movement limit in the vertical direction of the measurement unit 103, there is a case where movement of the measurement unit 103 stops halfway and alignment is not successful. Accordingly, the examiner D observes the anterior eye portion image 501 and adjusts a height of the jaw rest 104b as necessary.

The examiner D may instruct the examinee P to adjust the height of the jaw rest 104b by operating a jaw rest adjustment switch (not illustrated provided in the operation unit 101. For example, in FIG. 6, since the subject eye E is in a high state for the measurement unit 103, an instruction to lower the jaw rest 104b may be issued. If the examinee P operates the jaw rest adjustment switch, the control unit 107 moves the jaw rest 104b downwardly in response to an adjustment signal from the jaw rest adjustment switch. Further, if the examiner D observes the anterior eye portion image 501 displayed on the monitor 301 and confirms that a position of the subject eye E shown in the anterior eye portion image 501 is lowered, the examiner D may instruct the examinee P to perform the automatic alignment again.

Of course, the examiner D may adjust the height of the jaw rest 104b by operating the operation unit 302 of the remote operation unit 300 and selecting a jaw rest adjustment switch (not illustrated) displayed on the monitor 301. The control unit 303 of the remote operation unit 300 transmits the operation signal input from the jaw rest adjustment switch to the control unit 107 of the OCT device 100 via the shared server 400. The control unit 107 of the OCT device 100 moves the jaw rest 104b in the vertical direction in response to the received operation signal.

<Setting of Examination Condition>

If the alignment between the OCT device 100 and the subject eye E is completed, the examiner D sets a condition for starting examination of the subject eye E. The examiner D operates the operation screen 500 displayed on the monitor 301 to call a setting screen for setting an examination condition of the OCT device 100. Further, the examiner D operates the setting screen to set conditions such as a scanning position of measurement light and a scanning pattern (for example, line scan, raster scan, circle scan, radial scan, or the like) of the measurement light.

The control unit 303 of the remote operation unit 300 transmits a selection signal generated by selecting each condition to the control unit 107 of the OCT device 100 via the shared server 400. The control unit 107 of the OCT device 100 sets the examination condition of the OCT device 100 in response to the received selection signal.

In the present example, when the operation of the OCT device 100 is performed by one of the operation signal (first operation signal) that is generated by the operation of the operation unit 302 by the examiner D and the operation signal (second operation signal) that is generated by the operation of the operation unit 101 by the examinee P, performing the operation of the OCT device 100 by the other operation signal is prohibited. Accordingly, when the examiner D performs the setting operation, the examinee P is prohibited from performing the alignment operation or the jaw rest adjustment operation. For example, when the examiner D operates the operation unit 302, even if the examinee P operates the operation unit 101, an input of the operation signal by the operation unit 101 may be invalidated. For example, the fact that the input of the operation signal by the operation unit 101 is invalidated may be notified as a voice from a speaker (not illustrated).

<Start of Examination>

If the examination condition of the OCT device 100 is set, the examiner D starts examination of the subject eye E. For example, the examiner D operates the operation unit 302 to select an examination start switch (not illustrated) for starting examination of the OCT device 100 displayed on the monitor 301. The control unit 303 of the remote operation unit 300 transmits a start signal input from the examination start switch to the control unit 107 of the OCT device 100 via the shared server 400. The control unit 107 of the OCT device 100 starts examination by using the OCT device 100 in response to the received start signal. The control unit 107 may display a message indicating that imaging is started on a monitor (not illustrated) of the measurement unit 103 in response to the received start signal.

For example, the control unit 107 of the OCT device 100 performs an optimization control (for example, adjustment of an optical path length, adjustment of a focus, adjustment of a polarization state, and the like) for observing a fundus portion of the subject eye E that the examiner desires with a high sensitivity and a high resolution, and acquisition of OCT data, in response to the start signal. The control unit 107 of the OCT device 100 may generate a tomographic image of the subject eye E from the acquired OCT data, and transmit the tomographic image to the control unit 303 of the remote operation unit 300 via the shared server 400. At this time, the control unit 107 may transmit tomographic image to the control unit 303 in a state where a resolution of the tomographic image is lowered or the tomographic image is compressed if the tomographic image 502 is received, the control unit 303 may display the tomographic image 502 on the monitor 301. That is, the monitor 301 may display the tomographic image 502 of the subject eye E as the operation screen 500 of the OCT device 100. By observing the tomographic image 502 displayed on the monitor 301, the examiner D can easily examine the subject eye E even if the examiner is away from the examinee P.

For example, when imaging by the OCT device 100 is completed, a monitor (not illustrated) of the measurement unit 103 may be switched from a fixation target to a message indicating that imaging is completed.

<Display of Examiner Information>

The optometry system 1 according to the present example may present operator information (for example, information on the examiner D) for operating the OCT device 100 to the examinee P. For example, the operator information may be at least one of information such as a name and an affiliation of an operator and stored in the memory 402 of the shared server 400 in association with a user ID that the examiner D has individually.

Figure 7:
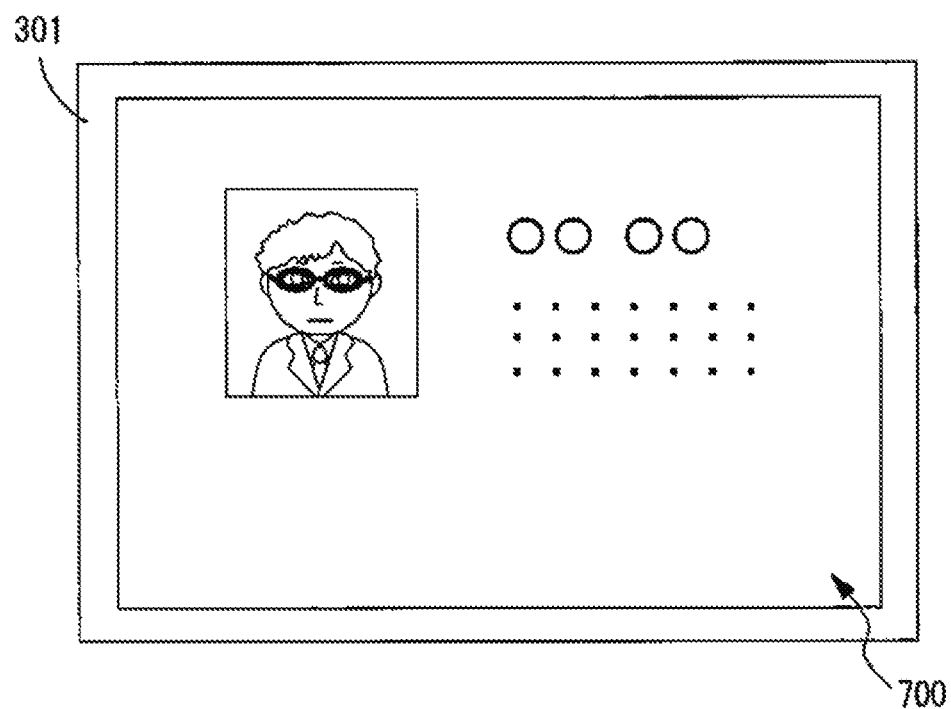
FIG. 7 is an example of operator information presented to an examiner.

FIG. 7 is an example of operator information 700 presented to the examinee P. For example, the examiner D inputs a user ID when using the remote operation unit 300. The control unit 303 of the remote operation unit 300 transmits the user ID to the control unit 401 of the shared server 400. When receiving the user ID, the control unit 401 calls the operator information corresponding to the user ID from the memory 402 and transmits the operator information to the control unit 107 of the OCT device 100. The control unit 107 may present the operator information to the examinee P by displaying the operator information on the monitor. The operator information 700 may be displayed on a monitor provided separately from the OCT device 100 or may be displayed on a monitor provided in the measurement unit 103 of the OCT device 100.

As described above, for example, the optometry system according to the present example includes an optometry device for examining the subject eye, an imaging unit that captures an image of an examination room including the examinee and the optometry device, and a remote operation unit that includes a display unit which displays an operation screen for operating the optometry device and the captured image captured by the imaging unit, and a display control unit that controls display of the display unit to display the operation screen and the captured image on the display unit. The remote operation unit enables the examiner to observe the captured image displayed on the display unit to guide the examinee to an examination position. As the optometry system has such a configuration, even if an examiner and the examinee are not in the same space, the examiner gives an appropriate instruction while observing the examinee to efficiently examine the subject eye.

Further, for example, the optometry system according to the present example displays an operation screen for operating the optometry device and the captured image captured by the imaging unit on the same screen of a display unit. Thereby, even if the examiner is not in the same space as the examinee, a series of actions of the examinee (for example, operations from when the examinee enters the examination room until the subject eye can be examined by using the optometry device, and the like) or a state of the examinee (for example, state during examination of the subject eye or the like) can be observed while operating the optometry device. Accordingly, it is possible to efficiently examine the subject eye.

Further, for example, in the optometry system according to the present example, the imaging unit includes a night vision camera that images an examination room under night vision and can image the examination room under the night vision. In a field of ophthalmology, a dark room is often made when examining the subject eye in order to reduce influence on an examination accuracy caused by a change in ambient light, such as a lighting apparatus in the examination room. By enabling imaging under night vision, a state of the examinee can be observed even in a dark room, and the subject eye can be accurately examined.

Further, for example, in the optometry system according to the present example, the optometry device includes a determination unit that determines whether or not the subject eye is in an examinable state and a first output unit that outputs determination information based on the determination result of the determination unit. For example, as the determination information is output, the examiner can easily grasp whether or not the examinee is in the examinable state.

Further, for example, in the optometry system according to the present example, the optometry device includes a determination unit that determines whether or not the subject eye is in an examinable state, and a second output unit that outputs an instruction signal for instructing a next operation to at least one of the optometry device and the remote operation unit based on a determination result of the determination unit. Thereby, the examiner can examination the subject eye efficiently.

Further, for example, in the present example, an imaging unit is disposed in an upper portion of the examination room in the examination room. According to this, the imaging unit easily images the entire examination room, and the examiner easily grasps a state of the examination room by using the captured image captured by the imaging unit. At this time, since the imaging unit is disposed in the upper portion and a corner of the examination room, the entire examination room is easily imaged even if a simple camera is used.

Further, for example, the optometry system according to the present example includes an optometry device that examines the subject eye, a first operation unit that is provided in a housing of the optometry device or near the optometry device and operates the optometry device, a second operation unit that is provided at a location spaced apart from the optometry device and operates the optometry device, a first setting unit that assigns a first operation of the optometry device to a first operation signal input from the first operation unit; and a second setting unit that assigns a second operation of the optometry device to a second operation signal input from the second operation unit. According to this, it is possible to assign an appropriate operation according to a location or skill of an operator (that is, an examiner, an examinee, an assistant, or the like) who operates the optometry device, content of an operation when examining the subject eye, and the like. Even if the examiner is not in a space where the optometry device is disposed, the examiner can easily examine the subject eye.

Further, for example, the optometry device according to the present example includes a fundus imaging unit that images a fundus of the subject eye, and at least one of the first setting unit and the second setting unit assigns an operation for starting imaging by the fundus imaging unit to the operation signal. For example, in the present example, the imaging start operation is assigned to the operation unit operated by the examiner, and the imaging start operation is not assigned to the operation unit operated by the examinee. Accordingly, even if an operation signal of imaging start is generated by the examinee, an abnormal operation of the optometry device is suppressed.

Further, for example, the optometry device according to the present example includes an alignment unit that aligns the subject eye and the optometry device, and at least one of the first setting unit and the second setting unit assigns an operation for performing alignment by the alignment unit to an operation signal. For example, in the present example, an alignment operation is not assigned to the operation unit operated by the examiner, and the alignment operation is assigned to the operation unit operated by the examinee. As the examinee who can grasp a sense of distance between a subject eye and a device performs the alignment operation, alignment can be performed safely.

Further, for example, the optometry system according to the present example includes an information acquisition unit that acquires operator information for operating the optometry device, a display unit that enables the operator information to be displayed, and a display control unit that displays the operator information on the display unit. According to this, even if an examiner and an examinee are not in the same space, the examinee can know information of the examiner and can be examined with peace of mind.

Modification Example

In the present example, a configuration in which the examinee P is guided by a voice of the examiner D is described as an example, but the present disclosure is not limited to this. For example, the examinee P may be guided by providing a lamp in the OCT device 100, a path to the OCT device 100, a chair, and the like and by turning on or blinking the lamp. The examiner D may confirm whether or not the examinee P is going to the OCT device 100 while viewing the captured image 600 displayed on the monitor 301 of the remote operation unit 300 and may give an appropriate instruction.

In the present example, a configuration in which the imaging unit 200 and the remote operation unit 300 are provided with a microphone and a speaker not illustrated) is described as an example, but the present disclosure is not limited to this. In the present example, voices of the examiner D and the examinee P may be able to be transmitted to each other. As an example, a configuration in which a microphone and a speaker are provided separately from the OCT device 100, the imaging unit 200, and the remote operation unit 300 may be used. As an example, the microphone and the speaker may be provided in the OCT device 100.

In the present example, a configuration in which the captured image 600 obtained by imaging the examination room 10 and the operation screen 500 for operating the OCT device 100 are simultaneously displayed on the monitor 301 of the remote operation unit 300 is taken as an example, but the present disclosure is not limited to this. For example, the captured image 600 and the operation screen 500 may be switched and displayed on a screen of the monitor 301. In this case, the control unit 107 of the OCT device 100 may switch between the captured image 600 and the operation screen 500 based on a switching signal for switching between the captured image 600 and the operation screen 500. For example, the switching signal may be generated when the examiner D operates a switching switch for switching between the captured image 600 and the operation screen 500. Further, for example, the switching signal may be generated by activating the OCT device 100 or the imaging unit 200, completing alignment, outputting an electrical signal by the detector 105, and the like.

For example, as described above, the optometry system according to the present example includes a signal acquisition unit that acquires a switching signal for switching between an operation screen for operating the optometry device and the captured image captured by the imaging unit, and a display control unit performs switching between the operation screen for operating the optometry device and the captured image captured by the imaging unit based on the switching signal to display on a screen of a display unit. The examiner can easily give an instruction to the examinee or easily examine a subject eye while observing the screen where the operation screen and the captured image are switched manually or automatically.

In the present example, a configuration in which the remote operation unit 300 includes the monitor 301 and the operation unit 302 is described as an example, but the present disclosure is not limited to this. For example, the remote operation unit 300 includes the monitor 301 but may be configured not to include the operation unit 302. In this case, the OCT device 100 may include a configuration for controlling a process from start of the alignment for the subject eye E to an end of the examination in a fully automatic manner (full automation). The examiner D guides the examinee P to the OCT device 100 while observing the captured image 600 displayed on the monitor 301, and the OCT device 100 may determine that the examinee P is in an examinable state and a fully automatic control may be performed.

In the present example, a case where the examiner D is in the operation room 20 and the examinee P is in the examination room 10 and the examiner D gives an instruction to the examinee P while observing the captured image 600 is taken as an example, but the present disclosure is not limited to this. For example, the examiner D is in the operation room 20, and the examinee and an assistant who assists the examinee P are in the examination room 10, and the examiner D may give an instruction to the assistant while observing the captured image 600. In this case, the examiner D may instruct the assistant to guide the examinee P, turn off and turn on electricity of the examination room 10, start alignment of the subject eye, adjust a jaw rest, and the like. Further, in this case, the examiner D may change assignment of various operations of the OCT device 100. For example, the operation unit 101 provided in the OCT device 100 may be used or the monitor 106 may be used as the operation unit operated by the assistant.

In the present example, a configuration in which all operations of the alignment operation are assigned to the operation unit 302 operated by the examiner D and the operation unit 101 operated by the examinee P is described as an example, but the present disclosure is not limited to this. A configuration in which at least a part of the alignment operation is assigned to the operation unit 302 and the operation unit 101 may be used. In more detail, a configuration in which a vertical operation for moving the measurement unit 103 in a vertical direction, a horizontal operation for moving the measurement unit 103 in a horizontal direction, and a front-rear operation for moving the measurement unit 103 in a front-rear direction are assigned to each unit may be used. Of course, operations assigned to the operation unit 302 and the operation unit 101 may overlap.

As an example, the vertical operation and the horizontal operation of the alignment operation are assigned to the operation unit 302 operated by the examiner D, and the front-rear operation of the alignment operation is assigned to the operation unit 101 operated by the examinee P (or an assistant). Further, as an example, the vertical operation and the horizontal operation of the alignment operation may be assigned to the operation unit 302 operated by the examiner D, and all the operations (that is, the vertical operation, the horizontal operation, and the front-rear operation) of the alignment operation may be assigned to the operation unit 101 operated by the examinee P (or an assistant).

In the present example, a configuration in which various operations of the OCT device 100 are not assigned to the operation unit 101 and the operation unit 302 and thereby setting of prohibiting input of an operation signal for performing various operations is performed is taken as an example, but the present disclosure is not limited to this. For example, a configuration in which the operation unit 101 and the operation unit 302 perform prohibition setting for prohibiting the performing of various operations of the OCT device 100 may be used.

In a case where such a prohibition setting is performed for the operation unit 101, as an example, input of an operation signal may be prohibited such that the operation signal from the operation unit 101 is not transmitted to the control unit 107. Further, as an example, the operation signal may be invalidated in a communication path between the operation unit 101 and the control unit 107 such that the control unit 107 does not receive the operation signal from the operation unit 101. Further, as an example, even if the control unit 107 receives the operation signal from the operation unit 101, a control may be made so as not to perform an operation based on the operation signal.

In a case where such prohibition setting is performed for the operation unit 302, as an example, the input of the operation signal may be prohibited such that the operation signal from the operation unit 302 is not transmitted to the control unit 303. Further, as an example, the operation signal may be invalidated in any of a communication path between the operation unit 302 and the shared server 400, or a communication path between the shared server 400 and the operation unit 101 such that the control unit 107 does not receive the operation signal from the operation unit 302. Further, as an example, even if the control unit 107 receives an operation signal from the operation unit 302, a control may be made so as not to perform an operation based on the operation signal.

For example, as described above, when an operation of an optometry device is performed by one of a first operation signal and a second operation signal, the optometry system according to the present example includes an operation control unit that prohibits performing of the operation of the optometry device by the other operation signal. According to this, switching to a control operation based on the other operation signal while the control operation based on one operation signal is being performed, is suppressed, and examination of a subject eye can be performed efficiently and safely.

In the present example, a configuration in which performing of an operation by the other operation unit is prohibited while one operation unit is used for the operation unit 302 operated by the examiner D and the operation unit 101 operated by the examinee P is described as an example, but the present disclosure is not limited to this. As an example, depending on the operation performed when the subject eye E is examined, performing of the operation by the operation unit 302 may be prioritized. That is, a configuration may be used in which even when a predetermined operation is being performed by the operation unit 101, performing of the operation by the operation unit 101 is prohibited by operating the operation unit 302, and the operation unit 302 is allowed to perform a predetermined operation. Of course, depending on the operation performed when the subject eye E is examined, performing of the operation by the operation unit 101 may be prioritized.

In the present example, a configuration in which the imaging unit 200 is provided in the examination room 10 is described as an example, but the present disclosure is not limited to this. For example, the imaging unit 200 may be provided in the OCT device 100. As an example, the imaging unit 200 may be stacked in an upper portion of the OCT device 100. As an example, the imaging unit 200 may be arranged in parallel on a side portion of the OCT device 100. In such a case, the imaging unit 200 may image the examination room 10 including an examinee.

What is claimed is:

1. An optometry system for examining a subject eye of an examinee, in an examination room, comprising:
    an optometry device installed in the examination room and configured to examine the subject eye;
    an imaging unit configured to capture an image of the examination room including the examinee and the optometry device to obtain a captured image to guide the examinee to the optometry device; and
    a remote operation unit including:
        a display unit configured to display an operation screen for operating the optometry device and the captured image captured by the imaging unit; and
        a display control unit configured to control display of the display unit to display the operation screen and the captured image on the display unit,
        wherein the remote operation unit enables an examiner to observe the captured image displayed on the display unit to guide the examinee to an examination position.

2. The optometry system according to claim 1,
    wherein the display control unit displays the operation screen and the captured image on the same screen of the display unit.

3. The optometry system according to claim 1, further comprising:
    a signal acquisition unit configured to acquires a switching signal for switching between the operation screen and the captured image,
    wherein the display control unit switches a screen to be displayed on the display unit between the operation screen and the captured image based on the switching signal.

4. The optometry system according to claim 1,
    wherein the imaging unit includes a night vision camera that images the examination room under night vision and enables the examination room to be imaged under the night vision.

5. The optometry system according to claim 1,
    wherein the optometry device includes:
        a determination unit configured to determine whether or not the subject eye is in an examinable state; and
        a first output unit configured to output determination information based on a determination result of the determination unit.

6. The optometry system according to claim 5,
wherein the optometry device includes:
   a jaw rest for placing a jaw of the examinee; and
   a detection unit configured to detect whether or not the jaw of the examinee is placed on the jaw rest,
   wherein the determination unit determines whether or not the subject eye is in an examinable state based on a detection result of the detection unit.

7. The optometry system according to claim 1,
wherein the optometry device includes:
   a determination unit configured to determine whether or not the subject eye is in an examinable state; and
   a second output unit configured to output an instruction signal for instructing a next operation to at least one of the optometry device and the remote operation unit based on a determination result of the determination unit.

8. The optometry system according to claim 1, wherein the imaging unit is disposed at an outside of a housing of the optometry device.

9. A non-transitory computer readable recording medium storing an optometry program executed in an optometry system for examining a subject eye of an examinee in an examination room,
   the optometry program is executed by a processor in the optometry system to cause the optometry system to perform:
   an imaging step of capturing an image of the examination room including the examinee and an optometry device installed in the examination room to obtain a captured image to guide the examinee to the optometry device;
   a display control step of controlling display of a display unit included in a remote operation unit to display an operation screen for operating the optometry device and the captured image captured by an imaging unit on the display unit; and
   a remote operation step of enabling an examiner to observe the captured image displayed on the display unit to guide the examinee to an examination position.

10. An optometry system for examining a subject eye of an examinee, comprising:
   an optometry device configured to examine the subject eye;
   a first operation unit comprising a first user interface provided in a housing of the optometry device or near the optometry device and configured to operate the optometry device;
   a second operation unit comprising a second user interface provided apart from the optometry device and configured to operate the optometry device;
   a first setting unit configured to assign a first operation of the optometry device to a first operation signal input from the first operation unit; and
   a second setting unit configured to assign a second operation of the optometry device to a second operation signal input from the second operation unit.

11. The optometry system according to claim 10, further comprising:
   an operation control unit configured to prohibit, when an operation of the optometry device according to one of the first operation signal and the second operation signal is performed, an operation of the optometry device according to the other of the first operation signal and the second operation signal from being performed.

12. The optometry system according to claim 10,
wherein the optometry device includes a fundus imaging unit configured to image a fundus of the subject eye, and
at least one of the first setting unit and the second setting unit assigns an operation for starting imaging by the fundus imaging unit to the operation signal.

13. The optometry system according to claim 10,
wherein the optometry device includes an alignment unit configured to align the subject eye and the optometry device, and
at least one of the first setting unit and the second setting unit assigns an operation for performing alignment by the alignment unit to the operation signal.

14. The optometry system according to claim 10, further comprising:
   an information acquisition unit configured to acquire operator information indicating an operator who operates the optometry device;
   a display unit configured to display the operator information; and
   a display control unit configured to cause the display unit to display the operator information.

* * * * *